(12) United States Patent
DiFoggio

(10) Patent No.: US 7,719,676 B2
(45) Date of Patent: May 18, 2010

(54) DOWNHOLE LASER MEASUREMENT SYSTEM AND METHOD OF USE THEREFOR

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 504 days.

(21) Appl. No.: 11/706,639

(22) Filed: Feb. 15, 2007

(65) Prior Publication Data

US 2008/0198375 A1 Aug. 21, 2008

(51) Int. Cl.
*G01J 3/00* (2006.01)

(52) U.S. Cl. .......................... 356/300; 356/73

(58) Field of Classification Search ............. 356/72–73, 356/301, 317–318
See application file for complete search history.

(56) References Cited

U.S. PATENT DOCUMENTS

| | | | |
|---|---|---|---|
| 3,641,457 A | 2/1972 | Brown et al. | |
| 3,947,781 A | 3/1976 | Hernqvist | |
| 4,206,422 A | 6/1980 | Fein et al. | |
| 4,227,582 A | 10/1980 | Price | |
| 4,402,574 A | 9/1983 | McConnel | |
| 4,752,936 A | 6/1988 | Gerhardt | |
| 5,059,256 A | 10/1991 | Kanapenas et al. | |
| 6,473,445 B1 | 10/2002 | Zeller | |
| 7,214,933 B2 * | 5/2007 | DiFoggio et al. | 250/269.1 |
| 7,511,813 B2 * | 3/2009 | Vannuffelen et al. | 356/328 |
| 7,530,265 B2 * | 5/2009 | DiFoggio | 73/152.42 |
| 2006/0086700 A1 | 4/2006 | Callies et al. | |
| 2007/0081157 A1 * | 4/2007 | Csutak et al. | 356/301 |
| 2007/0273852 A1 * | 11/2007 | Arai | 355/44 |

OTHER PUBLICATIONS

Douglas C. Sinclair and W. Earl Bell, Gas Laser Technology, Holt, Rinehart and Winston, Inc., 1969, USA.
Jacques Berlande, et al., Pressure and Electron Density Dependence of the Electron-Ion Recombination Coefficient in Helium, Physical Review A, Mar. 1970, p. 887-896, vol. 1, No. 3.

* cited by examiner

*Primary Examiner*—Kara E Geisel
(74) *Attorney, Agent, or Firm*—Charles S. Knobloch; Gordon T. Arnold; Arnold & Knobloch, L.L.P.

(57) ABSTRACT

A downhole laser measurement system useful for evaluating the chemical or elemental composition of geologic formations or formation fluids or interrogating a fiber optic sensor includes a pressure housing, wherein the pressure housing further includes a laser disposed in communication with a laser temperature control chamber; a laser light feedthrough; and an optical sensor array. An associated method of using a laser measurement system in a downhole well bore includes disposing a laser measurement system downhole in a well bore; using the laser to create a laser light, and then outputting the light to an optical sensor array.

19 Claims, 3 Drawing Sheets

DOWNHOLE LASER MEASUREMENT SYSTEM AND METHOD OF USE THEREFOR

FIELD OF THE INVENTION

The present invention relates generally to the downhole use of a laser measurement system in a well bore. Lasers possess unique abilities for performing optical spectroscopy to determine elemental or chemical composition. Lasers also possess unique abilities for interrogating fiber optic sensors to determine pressure or temperature. For example, a laser could be used to interrogate a Fabry-Perot pressure gauge, to create the plasma for laser-induced breakdown spectroscopy for elemental analysis, or to perform absorption or Raman-scattering optical spectroscopy for molecular chemical analysis. More specific, though non-limiting, embodiments include the downhole use of a vapor or gas laser in a well bore to determine the elemental or chemical composition of formation minerals or formation fluids or to operate a fiber optic sensor that measures pressure, temperature, strain or some other parameter.

BACKGROUND OF THE INVENTION

Well bores typically originate at or near the Earth's surface, and penetrate through one or more layers of the Earth's crust toward a predetermined depth or geologic formation. A variety of instrument systems have been used to estimate the elemental or chemical compositions of formations and formation fluids downhole using an uphole laser and a fiber optic transmission line downhole. Similarly, uphole lasers have been used to measure downhole temperature or pressure using a fiber optic sensor that is located downhole. Semiconductor lasers such as laser diodes are compact enough to be packaged within a tool that is lowered into a well bore. However, commercially available semiconductor lasers dim dramatically with increasing temperature and generally stop lasing altogether above approximately 125° C. Well bore temperatures usually exceed 125° C. and can even reach 200° C. or higher, making such devices unusable without cooling, which adds considerable complexity. To date, no satisfactory measurement system that uses a downhole laser has yet been realized.

While previously known laser instrument systems, for example, those employing optical or electromagnetic energy derived from a gaseous or vaporous laser source, have been used in the laboratory, there is no record of them being used downhole. To date, laser light is always generated at the surface (rather than being generated downhole) and then transported downhole over a long fiber optic cable.

The surface-based approach limits the use of lasers because a long fiber optic cable is always needed. For wireline logging, conventional logging cables usually consist of seven metallic wires (six individual wires wrapped around another), housed inside of an armored cable that can support a string of logging tools weighing around 14,000 pounds, or about half of the logging cable's breaking strength. Typically, these logging cables do not have a fiber optic disposed within. Difficulties associated with disposition of a fiber optic within a logging cable include backward compatibility with existing infrastructure, the tendency of optical fiber to snap when the logging cable is stretched under load, and the difficulty of field-splicing a broken logging cable if it were to contain an optical fiber. For logging-while-drilling (LWD), such a fiber optic cable would very likely be twisted and broken by a rotating drill string. The technology does not currently exist to incorporate a fiber optic cable into the drill string, as evidenced by the fact that LWD still uses mud pulse telemetry, which is extremely slow (10 to 50 baud) instead of a fiber optic cable, which is extremely fast (125 million baud).

There is, therefore, a longstanding need for a laser system that would allow laser-based measurements to be performed downhole, in which the need for a fiber optic line to the surface is obviated, and which would admit to a greater range of practical field application and measurement techniques.

SUMMARY OF THE INVENTION

A downhole laser measurement system useful for evaluating the composition of downhole samples is provided, the system including a pressure housing, wherein the pressure housing further includes a gaseous-state laser disposed in communication with a laser temperature control chamber; a laser light feedthrough; and an optical sensor or sensor array.

A method of using a laser measurement system downhole in a well bore is also provided, the method including disposing a laser downhole in a well bore; using the laser to create a laser emission; and outputting said emission to an optical sensor array.

DETAILED DESCRIPTION

Since high temperature is a primary limiting factor for employing a laser downhole, a gaseous-state laser can offer a practical solution. By design, the inside of gas or metal vapor laser is often held at high temperature and the lasing substance exists in the gaseous state. A vapor is simply the gaseous state of a substance that would normally be liquid or solid at room temperature. For metal vapor lasers the internal temperature is usually higher than the hottest well bore temperatures. For example, by design, the internal temperature of a helium-cadmium (HeCd) laser is approximately 250° C. An appropriate downhole laser measurement system useful for evaluating the chemical or elemental composition of formation minerals or fluid, or for interrogating a fiber optic sensor for pressure, temperature, or strain is therefore described herein, in which the system comprises a pressure housing; a laser disposed in communication with a laser temperature control chamber; a laser energy feed through; and an optical sensor array.

Figure 1:
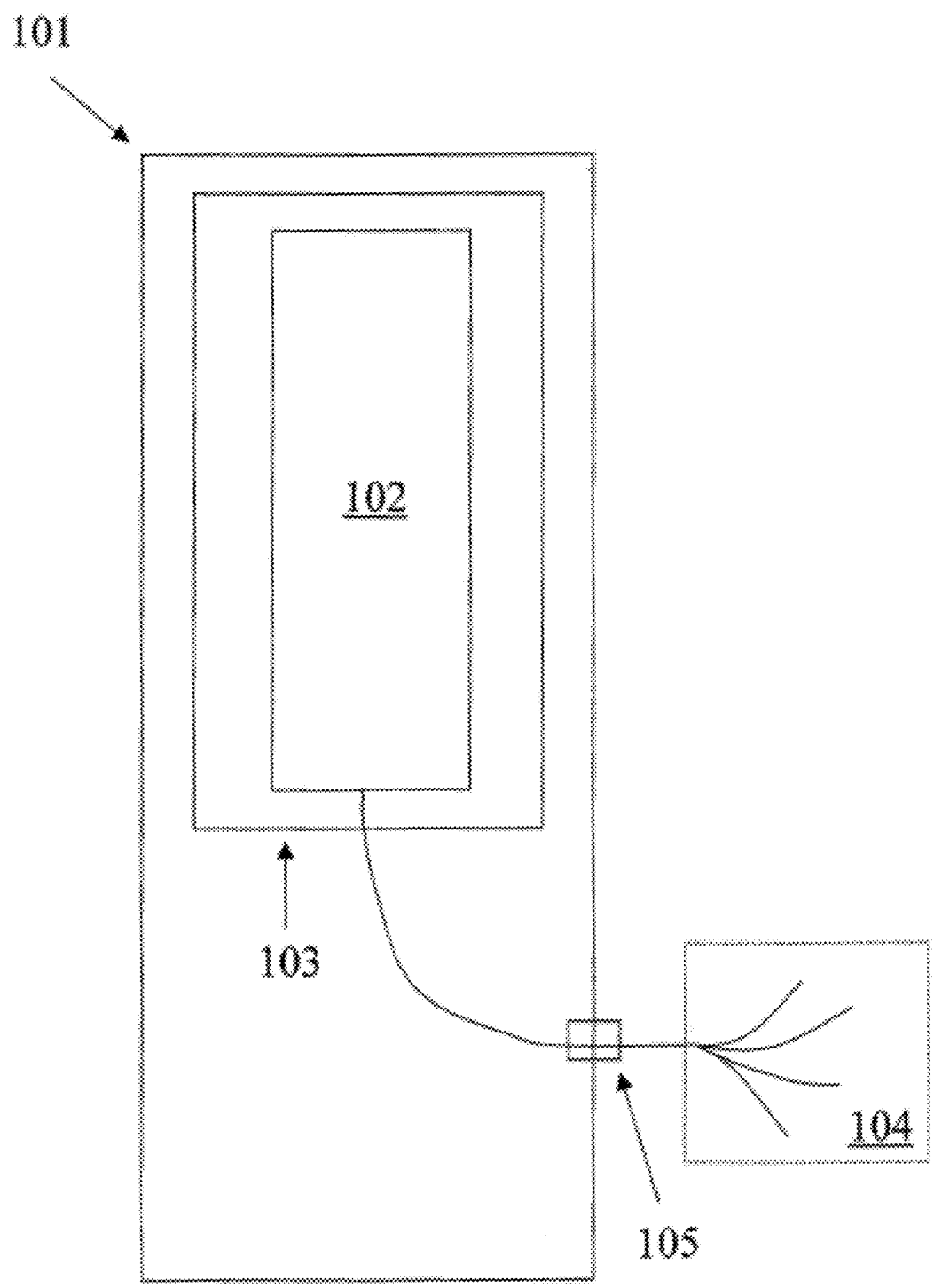
FIG. 1 is a schematic view of a downhole laser measurement system useful for measuring elemental or chemical composition or interrogating a fiber optic sensor according to an example embodiment of the invention.

Referring now to the example embodiment depicted in FIG. 1, a laser measurement system appropriate for downhole disposition in a well bore is provided, in which the system comprises a pressure housing 101, inside of which is housed a lasing device 102. In a presently preferred embodiment, lasing device 102 further comprises a gas or vapor laser, and resides within a temperature control chamber 103. In one embodiment, internal laser temperature is controlled by the amount of electrical current passing through the laser and by the surrounding temperature control chamber. In the depicted embodiment, laser light passes through a high-pressure feedthrough 105, e.g., an optical fiber high-pressure feedthrough, and then on to an optical sensor or sensor array 104.

When the internal laser temperature is higher than the ambient well bore temperature, the temperature control chamber 103 is not required to cool the laser, and will simply control the rate at which the laser's heat will flow to the colder well bore, such as with a heat pipe. Controlling heat flow from hot to cold is generally an easier task than pumping heat from cold to hot, as is done during active cooling.

In certain embodiments, laser 102 further comprises either an "atomic transition laser" or an "ion laser". In one example embodiment, the lasing action of an atomic transition helium-neon (HeNe) laser is produced by colliding electrons containing helium in order to create excited He atoms, followed by collisions of excited He atoms with Ne atoms. In contrast, ion lasers, such as argon or kryton lasers, typically use ionized gas as the lasing medium.

In one particular embodiment, a helium-neon mixture is used as an appropriate atomic transition lasing source. Helium-neon mixtures are known to emit at many different wavelengths in addition to the red wavelength typically used to evaluate the elemental composition of a formation. Therefore, one or more optical filters, for example, one or more filters disposed in communication with laser 102, are used to block the less useful wavelengths during spectroscopic analyses. By removing the filters, further spectroscopy is achieved using one or more of the previously blocked wavelengths for other spectroscopic analyses.

In other example embodiments, laser 102 further comprises an ionized metal vapor laser, or a neutral metal vapor laser, to create the lasing energy required for operations. Such lasers are presently preferred over gas lasers because of their ability to operate at higher temperatures, so long as those higher temperatures are carefully monitored and controlled by the laser temperature control chamber 103. Ionized and neutral metal vapor lasers also emit a variety of wavelengths, which are selectively blocked or unblocked by means of one or more filters disposed in communication with laser 102, or elsewhere within the system, for example, in communication with optical feedthrough device 105. In this manner, detailed spectroscopy is carried out in multiple stages in order to carefully evaluate the chemical or elemental composition of formation minerals or fluids.

In another detailed example of controlled neutral metal vapor lasing, copper vapor, or alternatively, gold vapor is used. An advantage of such devices is that both copper and gold vapor lasers have enjoyed rather extensive research and development efforts in association with other technical fields, and are generally considered at this time to be the most stable and commercially viable neutral metal vapor lasers. Both copper and gold vapor lasers emit light in the visible wavelength spectrum, and operate at high, sustained temperatures, thereby producing a relatively high power output. Such lasers also tend to be super-radiant, which enhances the reliability of certain measurement techniques. Moreover, copper and gold vapor lasers can be constructed of high-temperature resistant materials, for example, ceramic tubes, which make them particularly well suited for downhole application.

Figure 2:
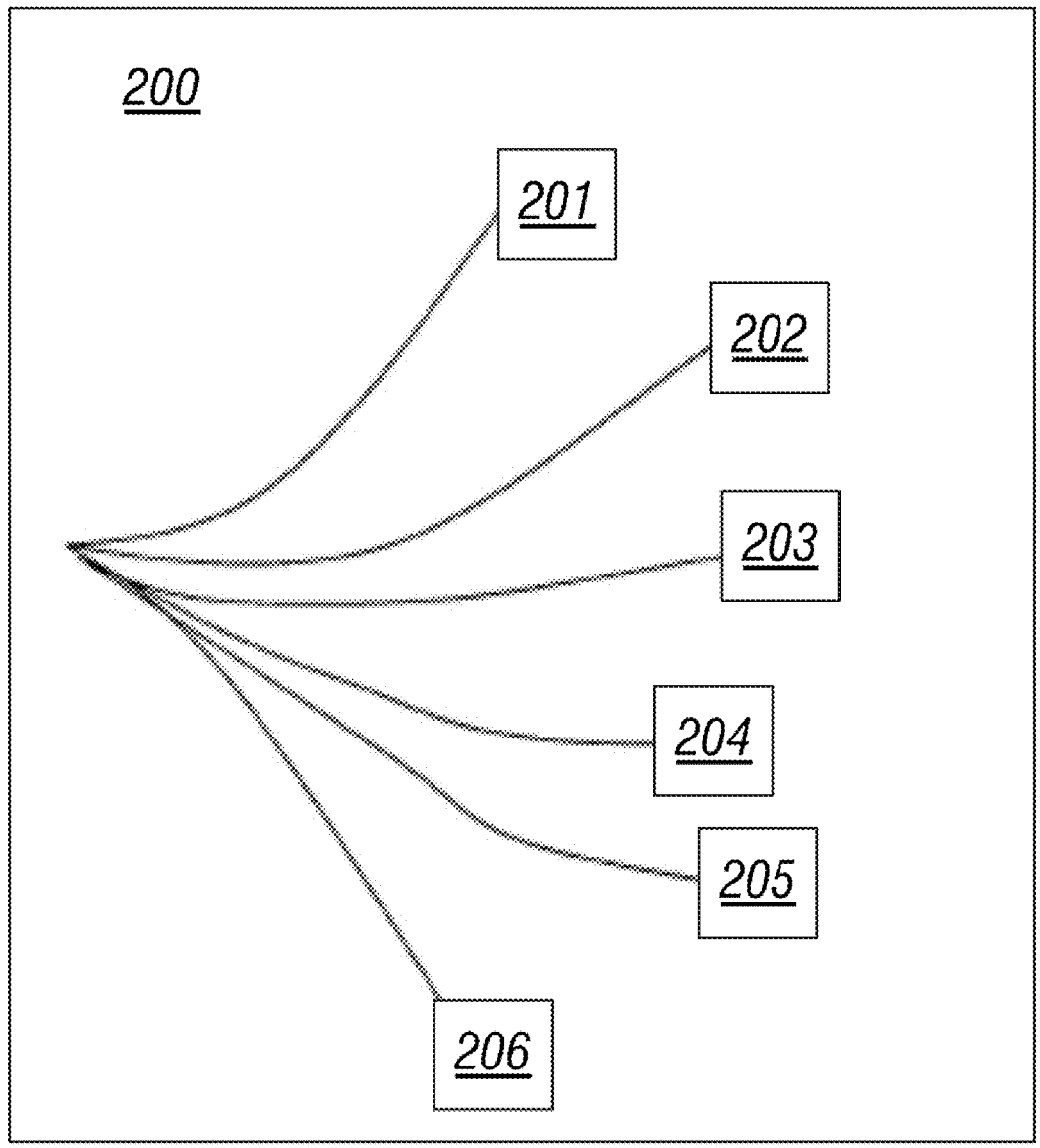
FIG. 2 is a more detailed view of the fiber optic sensor array depicted in FIG. 1 according to another example embodiment of the invention.

In certain embodiments, lasing light created by laser 102 is ultimately delivered to an optical sensor array 104, by means of a feedthrough or the like, for example, an optical fiber high pressure feedthrough 105. As seen in FIG. 2, optical sensor array 200 can be used to cooperatively employ one or more spectrographic detection and measurement devices. In one example embodiment, optical sensor array 200 is a fiber optic sensor array, though other similarly efficient devices can be employed within the scope of the claimed invention.

In another embodiment, the one or more spectrographic detection and measurement devices further comprises a Fabry-Perot pressure gauge 201 employed as measurement means. Such gauges detect pressure changes or a change in the physical path length present inside the gauge's light cavity, and/or a resulting change in the pattern of associated optical interference.

In further embodiments, a Fabry-Perot temperature sensor 202 is employed instead of, or in combination with, the aforementioned pressure sensor. In a still further embodiment, a fluorescence spectrometer 203 is employed, either alone or in combination with one or more of the Fabry-Perot sensors.

In a still further embodiment, an absorption spectroscopy sensor 204 is employed as a measurement means, the general advantages of which will be understood by those of skill in the art, with a particular advantage realized herein being the local generation of lasing energy down inside the well bore instead of at or near the Earth's surface as has been previously known.

In yet another example embodiment, a Raman spectroscopy sensor 205 is employed as a measurement means. In Raman spectroscopy, however, the emitted light signal is relatively dim. Accordingly, the light source must generally provide a very concentrated and substantially monochromatic light, as can best be achieved by using a laser light source.

In a further embodiment, a laser induced breakdown spectrometer 206 is employed as a measuring device. And in a still further embodiment, an optrode having a chemically sensitive coating (not shown) is included in the device. Optrodes are essentially fiber optic sensors, which have a chemically sensitive coating applied to either end (or both ends), so that light passing through the sensor will either change color or its refractive index when exposed to a predetermined, concentrated amount of that particular chemical.

According to further embodiments of the invention, one or more of the sensors contained within optical array 200 comprises a filter for selectively filtering certain wavelengths emitted by the lasing means. For example, known optical wavelength blocking filters can be used to select desired portions of the spectral bandwidth during a first measurement stage, and then removed to reveal a broader wavelength spectrum for measurement during a second measuring stage.

Figure 3:
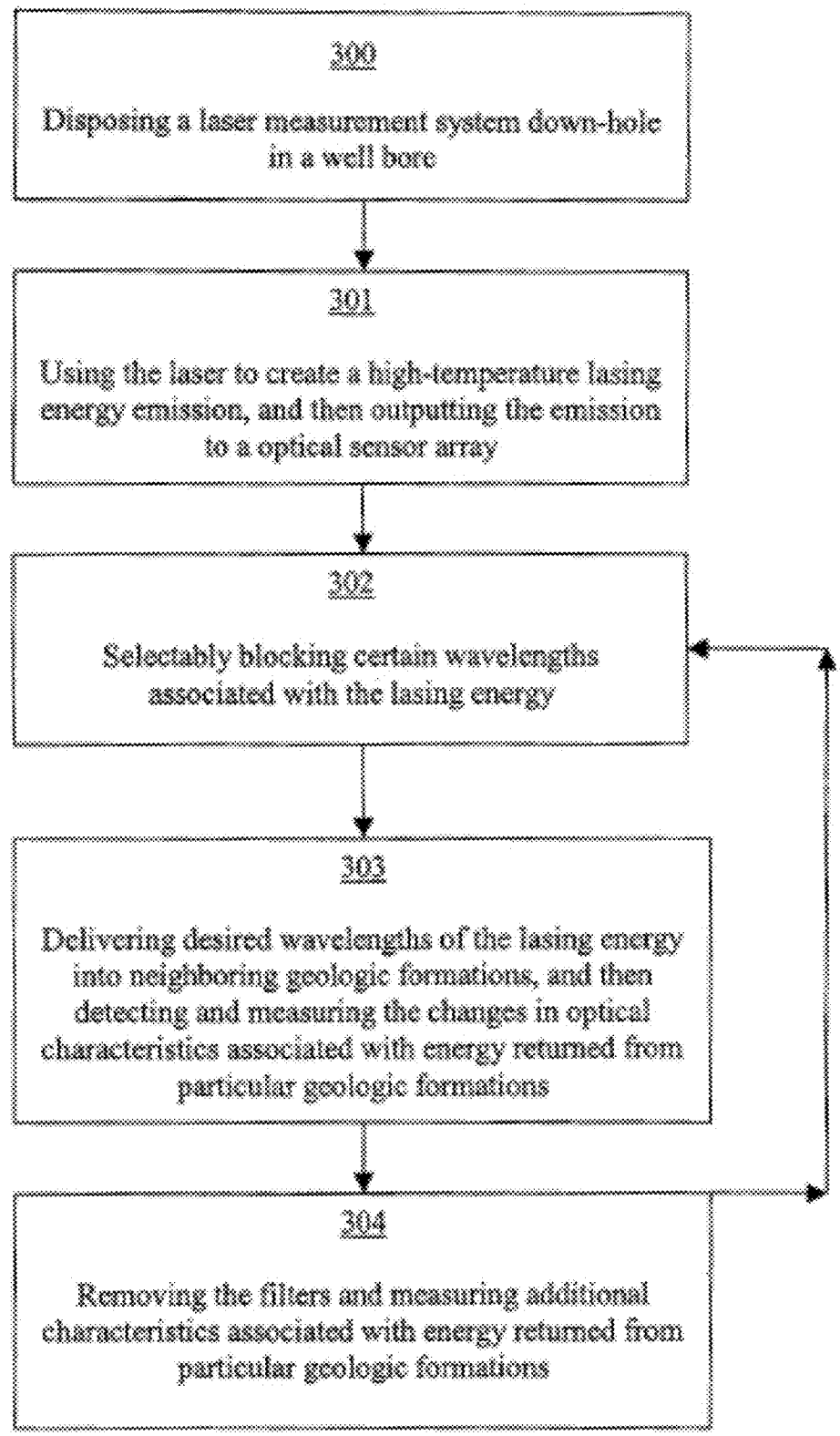
FIG. 3 shows a method of using a laser measurement system inside a well bore.

An associated method of using a laser measurement system inside a well bore is also contemplated, as shown in FIG. 3. In one particular embodiment, the method comprises first disposing a laser measurement system downhole in a well bore (step 300), using the laser to create a high-temperature lasing energy emission, and then outputting said emission to an optical sensor array (step 301).

A further example method of practicing the invention comprises delivering desired wavelengths of the lasing energy into neighboring regions, and then detecting and measuring the changes in optical characteristics associated with energy returned from particular formation minerals or fluids (step 303).

A further example method of practicing the invention comprises using a filter to selectably block certain wavelengths associated with the laser emissions prior to delivering the emission into formation minerals or fluids (step 302).

A still further example method of practicing the invention comprises removing the filter and then measuring additional characteristics associated with energy returned from particular formation minerals or fluids (step 304).

Known cabling, wire lines, drill stems, and placement methods can be used to dispose the laser measurement system in a desired downhole location within the well bore. Various spectrographic measurement devices and optical detection and measurement devices consistent with this disclosure can be used to detect, measure and interpret the chemical or elemental composition of formation minerals or fluid or to interrogate a fiber optic sensor.

The foregoing description is presented for illustrative purposes only, and is not intended to limit the invention to only the example embodiments described herein. Those of appropriate skill in the art will appreciate that various changes, modifications and omissions can be made without departing from either the scope or spirit of the invention claimed herein.

The invention claimed is:

1. A downhole laser measurement system useful for evaluating the composition of downhole samples, said system comprising:
   a pressure housing, wherein said pressure housing further comprises a gaseous-state laser disposed in communication with a laser temperature control chamber;
   a laser light feedthrough; and
   an optical sensor.

2. The system of claim 1, wherein said laser further comprises a gas laser.

3. The system of claim 1, wherein said laser further comprises a vapor laser.

4. The system of claim 1, wherein said gaseous-state laser further comprises a helium-neon atomic transition laser.

5. The system of claim 3, wherein said vapor laser further comprises an ionized metal vapor laser.

6. The system of claim 3, wherein said vapor laser further comprises a neutral metal vapor laser.

7. The system of claim 6, wherein said neutral metal vapor laser further comprises a copper vapor laser.

8. The system of claim 6, wherein said neutral metal vapor laser further comprises a gold vapor laser.

9. The system of claim 1, wherein said laser temperature control chamber further comprises an optical filter.

10. The system of claim 1, wherein said laser energy feed through further comprises an optical fiber high-pressure feedthrough.

11. The system of claim 1, wherein said laser energy feed through further comprises an optical filter.

12. The system of claim 1, wherein said optical sensor further comprises a Fabry-Perot pressure gauge.

13. The system of claim 1, wherein said optical sensor further comprises a Fabry-Perot temperature sensor.

14. The system of claim 1, wherein said optical sensor further comprises a fluorescence spectrometer.

15. The system of claim 1, wherein said optical sensor further comprises an absorption spectroscopy sensor.

16. The system of claim 1, wherein said optical sensor further comprises a Raman spectroscopy sensor.

17. The system of claim 1, wherein said optical sensor further comprises a laser induced breakdown spectrometer.

18. The system of claim 1, wherein said optical sensor further comprises an optrode.

19. The system of claim 1, wherein said optical sensor further comprises an optical filter.

* * * * *